US 9,962,843 B2

(12) United States Patent
Gester et al.

(10) Patent No.: US 9,962,843 B2
(45) Date of Patent: May 8, 2018

(54) METHOD FOR MEASURING FIBER CUTTING FORCE

(71) Applicant: The Gillette Company LLC, Boston, MA (US)

(72) Inventors: Matthias Gester, Farnborough (GB); Anthony William Shorey, Thatcham (GB)

(73) Assignee: The Gillette Company LLC, Boston, MA (US)

( * ) Notice: Subject to any disclaimer, the term of this patent is extended or adjusted under 35 U.S.C. 154(b) by 0 days. days.

(21) Appl. No.: 15/608,125

(22) Filed: May 30, 2017

(65) Prior Publication Data

US 2017/0368701 A1 Dec. 28, 2017

(30) Foreign Application Priority Data

Jun. 24, 2016 (EP) .................................. 16176220
Apr. 20, 2017 (EP) .................................. 17167200

(51) Int. Cl.
*G01N 19/02* (2006.01)
*B26B 21/40* (2006.01)
*G01L 5/00* (2006.01)
*G01N 3/58* (2006.01)

(52) U.S. Cl.
CPC ...... *B26B 21/4056* (2013.01); *B26B 21/4093* (2013.01); *G01L 5/0033* (2013.01); *G01L 5/008* (2013.01); *G01N 3/58* (2013.01)

(58) Field of Classification Search
CPC .. G01N 3/58; B26B 21/4081; B26B 21/4087; B26B 21/4093; G01L 5/0028; B23Q 17/09

USPC ............................................ 73/104–105, 159
See application file for complete search history.

(56) References Cited

U.S. PATENT DOCUMENTS

| 2,469,385 | A | * | 5/1949 | Hallock | ................... | G01N 3/58 |
| | | | | | | 73/104 |
| 4,178,797 | A | * | 12/1979 | Kozlowski, Jr. | ......... | G01N 3/58 |
| | | | | | | 73/104 |
| 4,528,843 | A | * | 7/1985 | Juranitch | ................. | G01N 3/58 |
| | | | | | | 73/104 |
| 5,181,416 | A | * | 1/1993 | Evans | ...................... | G01N 3/58 |
| | | | | | | 73/104 |
| 5,211,060 | A | | 5/1993 | O'Brien et al. | | |

(Continued)

FOREIGN PATENT DOCUMENTS

WO    WO 98/10694    3/1998
WO    WO 2011/109369    9/2011

OTHER PUBLICATIONS

European Search Report with Written Opinion in corresponding EPO Application 16176220.8 dated Dec. 21, 2016.

*Primary Examiner* — Jonathan Dunlap
(74) *Attorney, Agent, or Firm* — Kevin C. Johnson; Steven W. Miller

(57) ABSTRACT

A method and apparatus for measuring the cutting force on a single fiber. The method includes the steps of: providing a blade having an edge; providing a fiber mount for holding the single fiber; providing at least one sensor connected to the fiber mount; providing a fiber sleeve to contain a fiber within the fiber mount to simulate the location of the hair within the hair follicle; moving the blade toward the fiber and cutting the fiber; and measuring the cutting force on the fiber with the at least one sensor.

17 Claims, 6 Drawing Sheets

(56) References Cited

U.S. PATENT DOCUMENTS

| | | | | |
|---|---|---|---|---|
| 5,379,633 | A * | 1/1995 | Flisram | G01L 5/0028 73/104 |
| 5,571,956 | A * | 11/1996 | Sargent | G01N 3/58 73/104 |
| 7,293,451 | B2 * | 11/2007 | Dowd | G01N 3/58 73/105 |
| 7,344,498 | B1 * | 3/2008 | Doughty | A61B 5/0059 600/306 |
| 8,047,069 | B2 * | 11/2011 | Coulter | G01N 3/58 73/159 |
| 9,255,858 | B2 * | 2/2016 | Vallon | B26B 21/40 |
| 2006/0201237 | A1 * | 9/2006 | Dowd | G01N 3/58 73/104 |
| 2010/0300195 | A1 * | 12/2010 | Coulter | G01N 3/58 73/159 |
| 2011/0214493 | A1 * | 9/2011 | Vallon | B26B 21/40 73/104 |
| 2012/0123444 | A1 * | 5/2012 | Verhagen | A61B 18/20 606/133 |

\* cited by examiner

METHOD FOR MEASURING FIBER CUTTING FORCE

FIELD OF THE INVENTION

The present invention relates to a method and apparatus for measuring the cutting force on a single fiber, and more particularly, to a method for measuring the cutting force exerted by a blade on a single fiber such keratinous fibers, for example human hair.

BACKGROUND OF THE INVENTION

In general, many techniques have been used over the years to measure the cutting forces of a blade cutting different materials. For example, the wool felt cutter test measures the force on a blade as the blade cuts through wool felt. This method has worked satisfactorily over previous years for measuring the force on the blade as the blade cuts through the wool felt. However, the wool felt cutter test is only able to differentiate between blades when the differences in the cutting force exerted on the blades have relatively high measurable differences.

Another drawback with the wool felt cutter test is that it measures the force on the blade. The blade is held in a stationary position with a sensor attached to the blade. The wool felt is then moved across the blade edge to be cut. The sensor detects the force exerted on the blade as the blade edge cuts the wool felt.

In the wool felt cutter test, it is not known how many fibers are actually present in the wool felt. Furthermore, when the test is conducted it is not known how many fibers are actually cut by the blade and how far from the base the fibers have been cut.

Furthermore, in the wool felt cutter, blades have to remain static and dynamic cutting action like a sawing motion cannot be studied.

WO2011109369 describes a method for measuring the cutting force of a single fiber when cut by a blade. However, in order to accurately determine the cutting force representative of a shaving application, there is still a need to simulate the anchorage of the hair within the hair follicle in the skin, so that the effect on the cutting force can be determined.

There is also a need to prevent the fiber being pulled out of the fiber mount during the cutting process of the blade.

Moreover, there is also a need for a method and apparatus which enables rapid multiple cutting force measurements to be taken from a single fiber.

There is also a need to provide a method for measuring the cutting forces with a relatively high degree of sensitivity in order to determine the differences in the cutting forces between different blades.

There is a need to provide a method for measuring the cutting forces on different types of fibers.

There is a need to provide a method for measuring the cutting forces on hairs having different physiology and/or different chemical or mechanical treatment prior to cutting.

There is a need to provide a method for measuring the cutting force on hairs when the blades oscillate in specific direction, e.g. create a sawing, chopping or scraping movement, or with blades that are heated or electrically charged.

SUMMARY OF THE INVENTION

The present invention provides a method for measuring the cutting force on a single fiber. A blade having an edge is provided. A fiber mount for holding the fiber is provided. The single fiber to be tested is provided with a fiber sleeve which at least partially contains the fiber within the fiber mount and preferably beyond the fiber mount. At least one sensor connected to the fiber mount is provided. The blade is moved toward the fiber and cuts the fiber. The cutting force on the fiber is measured with the sensor.

The fiber mount may comprise a fiber mount inlet through which the fiber and optionally the fiber sleeve may be fed into the fiber mount. The fiber mount may also comprise a fiber mount outlet through which the fiber and optionally the fiber sleeve exits the fiber mount. The fiber mount outlet may have a shape selected from the group of circular, square, triangular, oval, and rectangular, preferably circular. The fiber may extend from the fiber mount outlet by a distance from about 0.01 mm to about 2.0 mm prior to being cut.

The fiber mount may comprise a trough which is able to hold a fluid. The fluid may alter or modify the chemical or mechanical properties of the fiber prior to cutting. The fluid may be water.

The fiber sleeve may have a fiber sleeve outlet through which the fiber exits the fiber sleeve. The fiber sleeve outlet may be coincident with the fiber mount outlet or extend beyond the fiber mount outlet. The fiber sleeve may have a tubular shape and a circular outlet. The fiber sleeve may be resilient. The fiber sleeve may be permeable to fluids contained in the trough, if present, in the fiber mount.

A blade mount to hold the blade may be provided. The blade mount can be moved to cut the fiber with different portions of the edge. The blade mount may be dimensioned to hold at least one blade, preferably at least two blades. The blade mount can hold the blade at different angles with respect to the fiber mount.

The apparatus may comprise multiple sensors. The multiple sensors measure cutting forces in multiple directions.

The apparatus may contain actuators on the blade mount to create additional blade motion or may contain electrically connections to heat or electrically charge the blade.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION OF THE INVENTION

Figure 1:
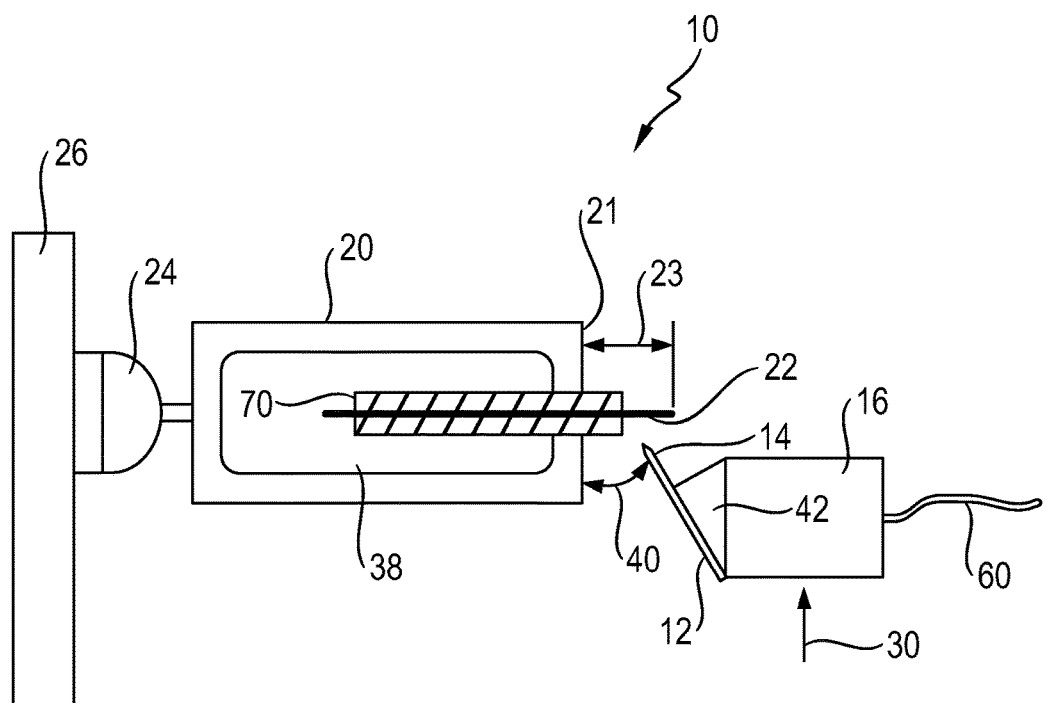
FIG. 1 is a top plan view of a fiber cutting apparatus of the present invention.

A cutting apparatus 10 for measuring the cutting force on a single fiber is shown in FIG. 1. The cutting apparatus 10 includes a blade 12 having an edge 14. The blade 12 may be supported or held by a blade mount 16. The cutting apparatus 10 includes a fiber mount 20 for holding said single fiber 22. A sensor 24 is connected to the fiber mount 20. The sensor 24 is shown mounted to a fixture 26. The fiber is at least partially, preferably is entirely contained within a fiber sleeve 70 and the fiber sleeve is at least partially contained within the fiber mount (20). The fiber mount may have a fiber mount inlet (not shown). The fiber mount may have a fiber mount outlet (50). During operation of apparatus 10, blade mount 16 moves linearly in direction 30 towards fiber 22 moving blade 12 towards fiber 22 until blade 12 cuts fiber 22. As blade 12 cuts fiber 22 sensors 24 measures the cutting force exerted by blade 12 on fiber 22. The blade does not cut the fiber sleeve 70.

The fiber mount 20 may include a trough 38. Trough 38 may be configured to hold water or other fluids and/or liquids. For example, trough 38 may hold shave creams and shave preparation or any other chemistry to modify the hair properties prior to cutting. Water may be added to trough 38 to hydrate the fiber 22 prior to being cut by blade 12. The trough may also contain another fluid including detergents, dye, salt solution, wax, a micro- or nano-particle suspension or others that modify and/or alter the chemical or mechanical properties of the fiber prior to cutting.

Different types of single fibers may be cut with apparatus 10. Examples of such fibers include but are not limited to keratinous fibers such as head hair, beard hair, leg hair, and nylon, thread, yarn, wool, synthetic fibers, natural fibers, carbon fibers, monofilament fibers, bi-component or multi-component fibers, etc. Fibers of different diameters or cross sections may also be cut with apparatus 10.

The blade mount 16 can be adjusted to hold blade 12 at different angles 40 with respect to fiber mount 20. For example, blade mount 16 may include a blade support 42. Blade supports 42 having different shapes may be used to position blade 12 at different angles 40 with respect to fiber mount 20.

The blade mount 16 may be connected to a power source via power supply cable 60 to provide power to blade mount 16. With the available power the blade mount 16 may be equipped to heat the blade 12. The blade mount 16 may be equipped to electrically charge blade 12. The blade mount 16 may oscillate in a specific direction to create a sawing, chopping or scraping movement by blade 12 with respect to fiber 22.

The fiber 22 is at least partially contained, preferably is substantially contained within a fiber sleeve 70 and the fiber sleeve 70 is at least partially contained within the fiber mount 20. The fiber sleeve 70 may be resilient. The fiber sleeve may be comprised of materials such as silicone, nitrile, polychloroprene, natural rubber and mixtures thereof. The fiber sleeve 70 may have a Shore A hardness of from 20 to 90. The fiber sleeve 70 may preferably have a tubular or substantially tubular shape. The fiber sleeve 70 may have an inner diameter of from about 0.05 mm to about 0.5 mm or from about 0.1 mm to about 0.3 mm. The fiber sleeve 70 may have a uniform diameter. The fiber sleeve 70 may have a fiber sleeve inlet (not shown) where the fiber 22 enters the fiber sleeve 70. The fiber sleeve 70 may also have a fiber sleeve outlet 72 where the fiber 22 exits the fiber sleeve 70.

Figure 5:
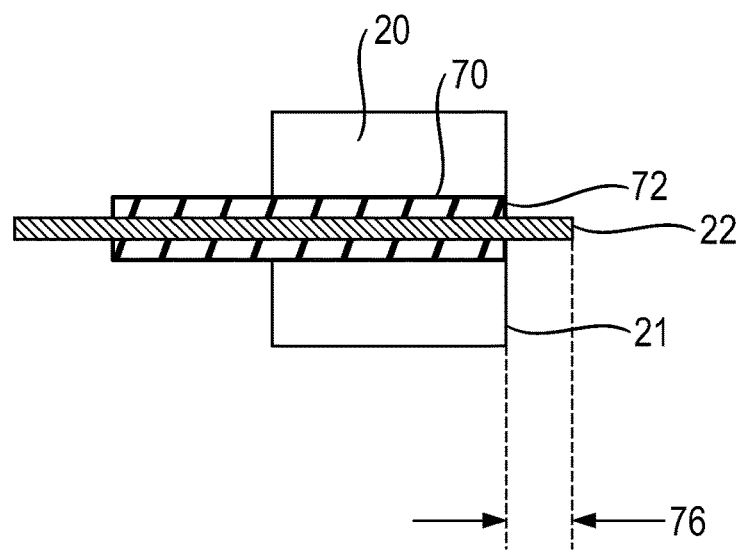
FIG. 5 is a side view of a fiber mount of the present invention.
Figure 6:
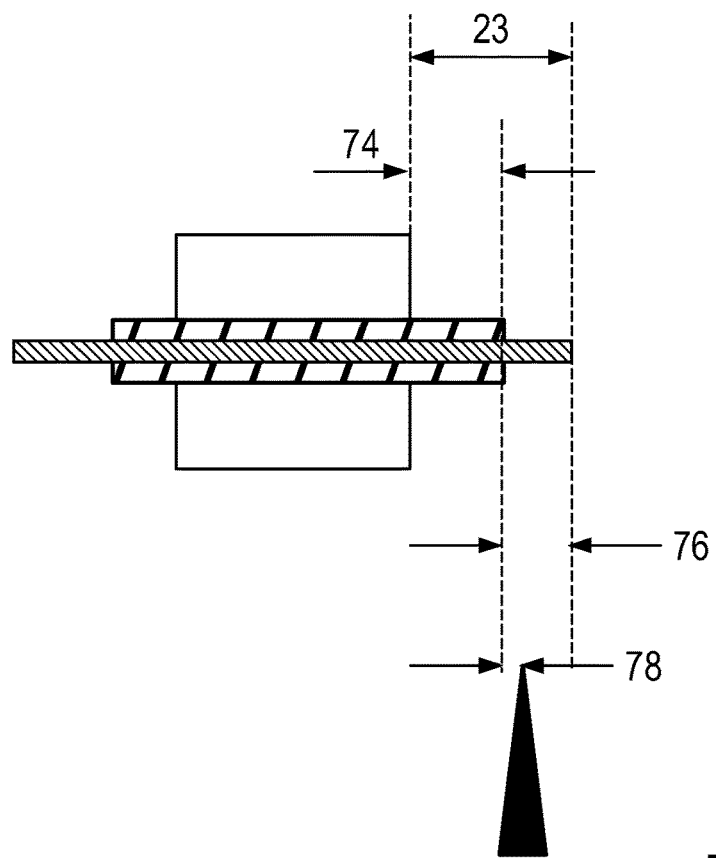
FIG. 6 is a side view of another embodiment of a fiber mount of the present invention.

Referring now to FIGS. 1, 5 and 6, the fiber sleeve 70 and/or fiber sleeve outlet 72 may extend beyond the fiber mount front face 21 or may be coincident therewith. While not being bound by theory it is believed that the presence of the fiber within the fiber sleeve simulates how a keratinous fiber is contained within the hair follicle and skin and allows the fiber to move laterally i.e. substantially in the direction 30 and or rotate around its longitudinal axis as it comes into contact with the blade. This provides a more accurate evaluation of the fiber cutting force on a single fiber in vivo in the skin by a cantilever mechanism such as by a shaving blade. Lateral movement of the fiber 22 can be adjusted by varying the distance 74 by which the fiber sleeve 70 extends from the fiber mount front face 21 and/or varying the distance 76 by which the fiber 22 extends from the fiber sleeve outlet 72 or both represented as distance 23.

The fiber 22 may extend from the fiber mount 20 by a distance 23 of from about 0.01 mm, 0.05 mm, 0.1 mm, 0.2 mm, 0.3 mm, 0.4 mm and 0.5 mm to about 1.0 mm, 2.0 mm, 3.0 mm, 4.0 mm and 5.0 mm. Preferably the fiber 22 extends from the fiber mount 20 by a distance 23 of from about 0.2 mm to about 2.0 mm. The fiber may extend from the fiber sleeve outlet 72 by a distance 76 of from about 0.01 mm, 0.05 mm, 0.1 mm, 0.2 mm, 0.3 mm, 0.4 mm and 0.5 mm to about 1.0 mm, 2.0 mm, 3.0 mm, 4.0 mm and 5.0 mm. Preferably, the fiber 22 extends from the fiber sleeve outlet 72 by a distance 76 of from about 0.2 mm to about 2.0 mm.

The blade 12 may be positioned relative to the fiber sleeve outlet 72 to cut the fiber 22 at a distance 78 of from about 0.01 mm, 0.5 mm, 0.1 mm, 0.2 mm, 0.3 mm, 0.4 mm and 0.5 mm to about 1.0 mm, 2.0 mm, 3.0 mm, 4.0 mm and 5.0 mm. Preferably, the blade is positioned at a distance 78 of from about 0.2 mm to about 2.0 mm.

Figure 2:
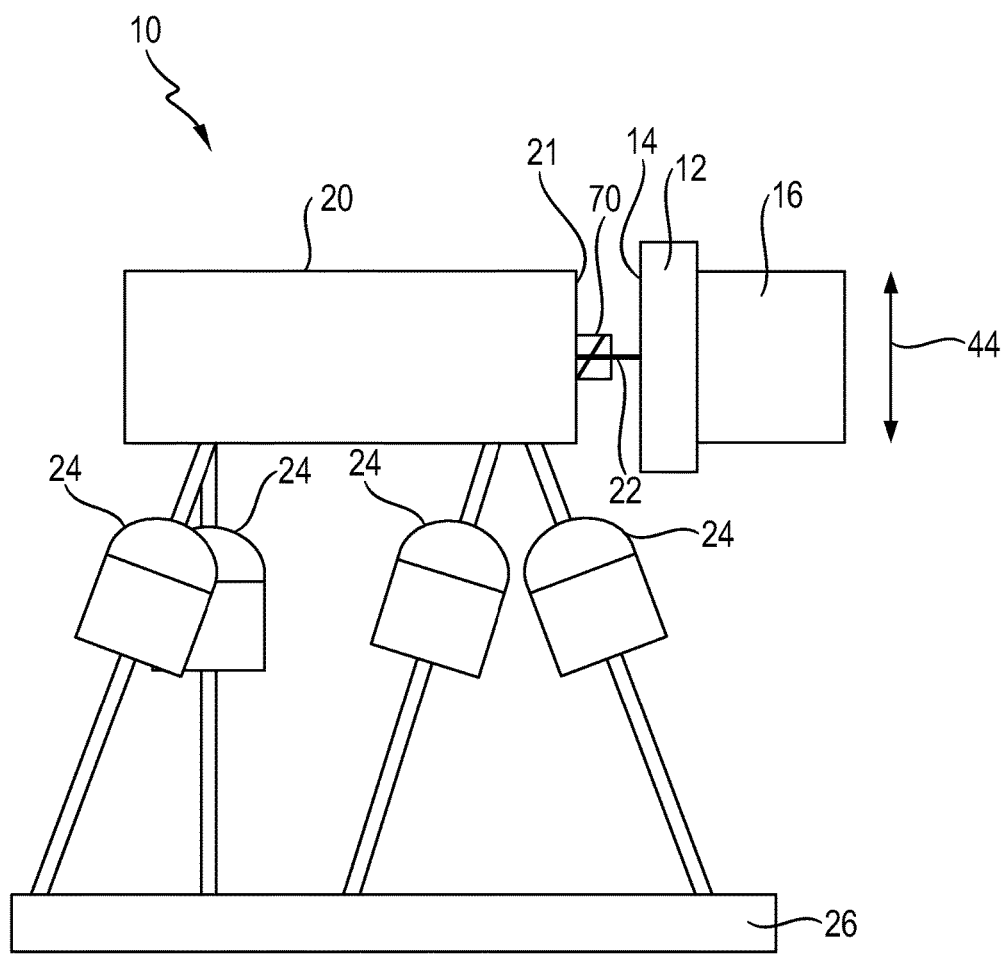
FIG. 2 is a side view of another fiber cutting apparatus of the present invention.

Another cutting apparatus 10 for measuring the cutting force on a single fiber is shown in FIG. 2. The cutting apparatus 10 includes a blade 12 having an edge 14. The blade 12 may be supported or held by a blade mount 16. The cutting apparatus 10 includes a fiber mount 20 for holding said fiber 22. Pluralities of sensors 24 are connected to the fiber mount 20. The sensors 24 are shown mounted to a fixture 26. Apparatus 10 is shown with four sensors 24. Apparatus may have any number of sensors. For example, apparatus 10 may have one, two, three, four, or more sensors 24. Sensors 24 measure cutting forces in multiple directions different from one another on the single fiber. The fiber 22 is contained within a fiber sleeve 70 in the fiber mount 20 which extends beyond the fiber mount front face 21. During operation of apparatus 10, blade mount 16 moves linearly towards fiber 22 moving blade 12 towards fiber 22 until blade 12 cuts fiber 22. As blade 12 cuts the fiber 22, sensors 24 measure the cutting forces exerted by blade 12 on the fiber 22.

The fiber mount 20 may include a trough such as trough 38 shown in FIG. 1. The blade mount 16 can be adjusted to hold blade 12 at different angles with respect to fiber mount 20 as discussed with respect to FIG. 1.

Figure 3:
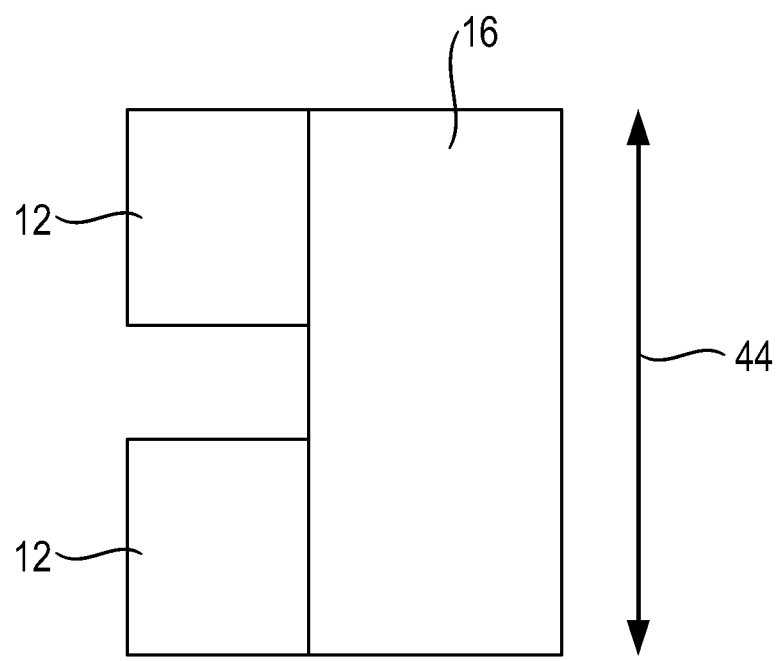
FIG. 3 is a side view of a blade mount of the present invention holding two blades.

The blade mount 16 can be moved in a direction indicated by arrow 44 to cut the fiber 22 with different portions of the blade 14. Referring now to FIG. 3, blade mount 16 is shown holding two blades 12. Blade mount 16 may hold more than two blades 12. For example, blade mount 16 may hold three, four, or more blades 12. Blade mount 16 can be moved in a direction indicated by arrow 44 to first cut a fiber with one blade and then cut a fiber with the other blade.

Figure 4:
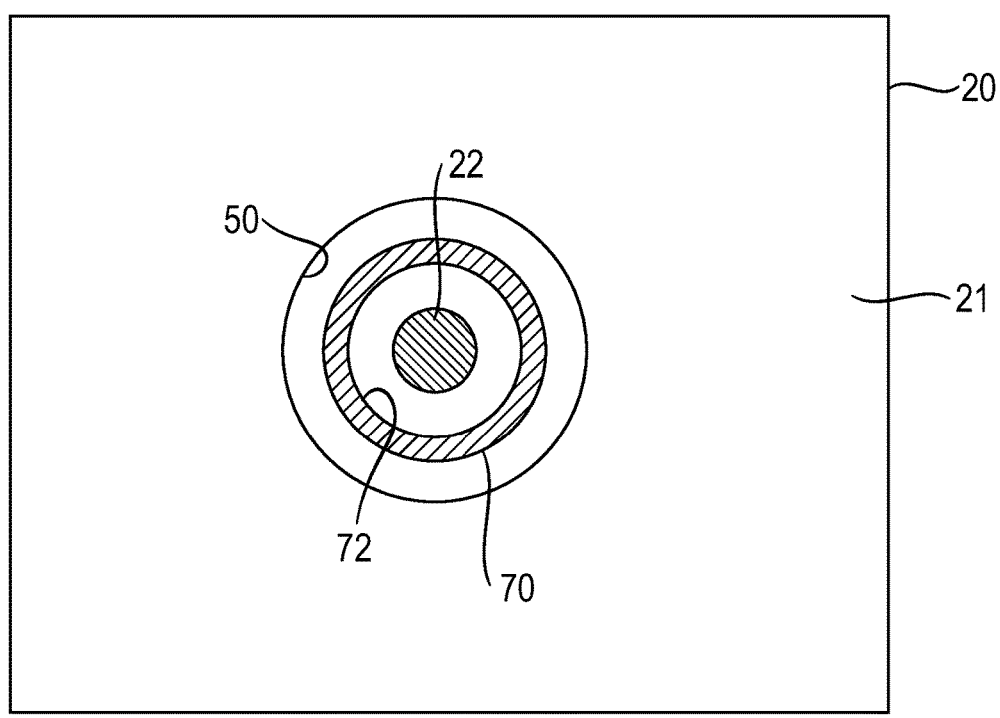
FIG. 4 is a front view of a fiber mount of the present invention.

Referring now to FIGS. 1, 2, 4 and 5, fiber mount 20 has a front face 21 from which fiber sleeve 70 extends. Front face 21 has a fiber mount outlet 50 through which fiber sleeve 70 is fed. In FIG. 4, fiber mount outlet 50 is shown to have a circular shape. Other shapes such as square, triangular, oval, and rectangular may be used for fiber mount outlet 50.

Figure 7A:
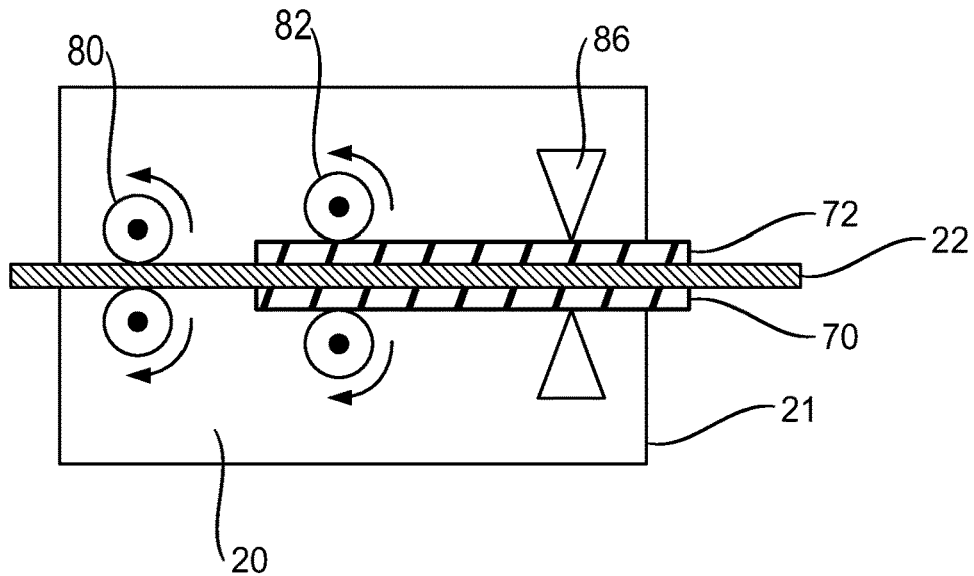
FIGS. 7a and 7b are partial side views of two further embodiments of a fiber mount of the present invention.
Figure 7B:
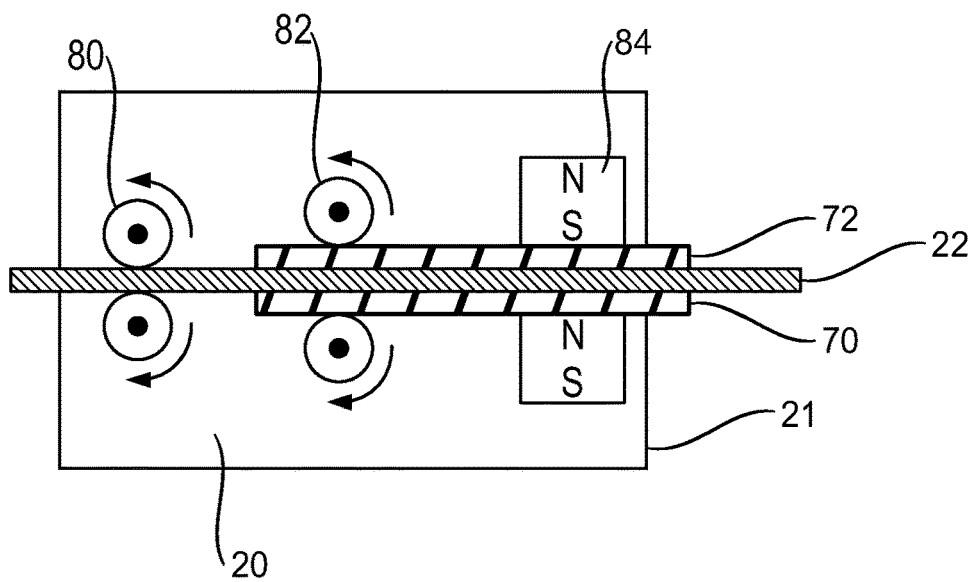

Referring to FIGS. 7a and 7b, the fiber 22 may be fed through the fiber sleeve outlet 72 either manually or automatically. Preferably, the fiber 22 and/or fiber sleeve 70 may be secured in the fiber mount by a securing means such as clamps 86, or fiber and fiber sleeve rollers 80, 82, pads or magnets 84 or other devices or combinations thereof, while the fiber 22 is cut by blade 12. The fiber 22 and/or fiber sleeve 70 may be clamped rigidly. Alternatively, the fiber 22 and fiber sleeve 70 may be held between two deformable pads, such as rubber or elastic pads, to further simulate the manner in which hair is embedded in skin tissue.

The fiber 22 is shown to extend from the fiber sleeve outlet 72 substantially perpendicular to front face 21. Fiber 22 may be positioned to extend from fiber mount 20 at various angles with respect to front face 21.

The fiber sleeve 70 may have an outlet 72 which may be coincident with the fiber mount front face 21 as shown in FIG. 5. Alternatively, the fiber sleeve outlet 72 may extend beyond the fiber mount front face 21 as shown in FIG. 6. The fiber sleeve may extend beyond the fiber mount front face 21 by a distance 74 as shown in FIG. 6. The distance 74 is believed to equate to the softness of the skin. Thus, increasing the distance 74 is equivalent to "softening the skin" in which the fiber 22 is held.

Combinations:

An example is below:
1. A method for measuring the cutting force on a single fiber, said method comprising the steps of:
   a. providing a blade having an edge;
   b. providing a fiber mount for holding said fiber; wherein said fiber mount comprises a fiber sleeve to contain said fiber in said fiber mount;
   c. providing at least one sensor connected to said fiber mount;
   d. moving said blade toward said fiber and cutting said fiber; and
   e. measuring the cutting force on said fiber with said sensor.
2. The method of Paragraph A, wherein said fiber sleeve is resilient.
3. The method of Paragraph A, wherein said fiber sleeve has a fiber sleeve outlet.
4. The method of Paragraph A, wherein said fiber mount comprises a fiber mount outlet.
5. The method of Paragraphs C and D, wherein said fiber mount outlet is coincident with said fiber sleeve outlet.
6. The method of Paragraph D, wherein said fiber mount has a fiber mount front face, wherein said fiber sleeve extends beyond said fiber mount outlet and said fiber mount front face.
7. The method of Paragraphs C and D, wherein said fiber extends from said fiber mount outlet and/or fiber sleeve outlet by a distance of from about 0.01 mm to about 2.0 mm prior to being cut.
8. The method according to Paragraph A, wherein said fiber sleeve is substantially tubular.
9. The method according to Paragraph A, wherein said fiber sleeve has an inner diameter of from 0.05 mm to 0.5 mm
10. The method according to Paragraph A, wherein said fiber sleeve comprises a material selected from silicone, nitrile, polychloroprene, natural rubber, and mixtures thereof.
11. The method according to Paragraph A, wherein said fiber sleeve has a Shore A hardness of from 20 to 90.
12. The method according to Paragraph A, wherein said fiber mount comprises a securing means, preferably selected from a clamp, magnet, roller, pad or a combination thereof.
13. The method according to Paragraph C, wherein said fiber can be fed through said fiber sleeve to said fiber sleeve outlet, preferably by rollers.
14. The method according to Paragraphs C and D, wherein said fiber sleeve can be fed through said fiber mount to said fiber mount outlet, preferably by rollers.
15. The method according to any one of Paragraphs A-O wherein said fiber is a keratinous fiber.
16. The method of Paragraph A, further comprising the step of providing a blade mount to hold said blade.
17. An apparatus to measure the cutting force of a fiber with a blade, said apparatus comprising a blade and a fiber mount wherein said fiber mount comprises a fiber sleeve and a sensor connected to said fiber mount, wherein said mount further comprises a fiber mount outlet and said fiber sleeve has a fiber sleeve outlet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition of the same term in a document incorporated by reference, the meaning of definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for measuring the cutting force on a single fiber, said method comprising the steps of:
   a. providing a blade having an edge;
   b. providing a fiber mount for holding said fiber; wherein said fiber mount comprises a fiber sleeve to contain said fiber in said fiber mount;
   c. providing at least one sensor connected to said fiber mount;
   d. moving said blade toward said fiber and cutting said fiber; and
   e. measuring the cutting force on said fiber with said sensor.
2. The method of claim 1, wherein said fiber sleeve is resilient.
3. The method of claim 1, wherein said fiber sleeve has a fiber sleeve outlet.

4. The method according to claim 3, wherein said fiber can be fed through said fiber sleeve to said fiber sleeve outlet, preferably by rollers.

5. The method of claim 1, wherein said fiber mount comprises a fiber mount outlet.

6. The method of claim 5, wherein said fiber mount outlet is coincident with said fiber sleeve outlet.

7. The method of claim 5, wherein said fiber mount has a fiber mount front face, wherein said fiber sleeve extends beyond said fiber mount outlet and said fiber mount front face.

8. The method of claim 5, wherein said fiber extends from said fiber mount outlet and/or fiber sleeve outlet by a distance of from about 0.01 mm to about 2.0 mm prior to being cut.

9. The method according to claim 5, wherein said fiber sleeve can be fed through said fiber mount to said fiber mount outlet, preferably by rollers.

10. The method according to claim 1, wherein said fiber sleeve is substantially tubular.

11. The method according to claim 1, wherein said fiber sleeve has an inner diameter of from 0.05 mm to 0.5 mm.

12. The method according to claim 1, wherein said fiber sleeve comprises a material selected from silicone, nitrile, polychloroprene, natural rubber, and mixtures thereof.

13. The method according to claim 1, wherein said fiber sleeve has a Shore A hardness of from 20 to 90.

14. The method according to claim 1, wherein said fiber mount comprises a securing means, preferably selected from a clamp, magnet, roller, pad or a combination thereof.

15. The method according to claim 1, wherein said fiber is a keratinous fiber.

16. The method of claim 1, further comprising the step of providing a blade mount to hold said blade.

17. An apparatus to measure the cutting force of a fiber with a blade, said apparatus comprising a blade and a fiber mount wherein said fiber mount comprises a fiber sleeve and a sensor connected to said fiber mount, wherein said mount further comprises a fiber mount outlet and said fiber sleeve has a fiber sleeve outlet.

* * * * *